US006198020B1

(12) United States Patent
Bowen et al.

(10) Patent No.: US 6,198,020 B1
(45) Date of Patent: Mar. 6, 2001

(54) NITRIC OXIDE AS AN ACTIVATOR OF THE PLANT PATHOGEN DEFENSE SYSTEMS

(75) Inventors: Benjamin A. Bowen; Jonathan P. Duvick; Carl R. Simmons, all of Des Moines, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/257,541

(22) Filed: Feb. 24, 1999

Related U.S. Application Data

(60) Provisional application No. 60/076,153, filed on Feb. 26, 1998.

(51) Int. Cl.[7] .............................. A01H 1/00; A01H 9/00; C12N 15/82; C12N 15/87; C12N 5/00
(52) U.S. Cl. .................... 800/278; 435/410; 435/419; 800/278; 800/286; 800/290; 800/295; 800/279; 800/300.1; 800/320.1
(58) Field of Search ..................... 435/410, 419; 800/278, 286, 290, 295, 279, 300.1, 320.1

(56) References Cited

U.S. PATENT DOCUMENTS

| 5,367,065 | 11/1994 | Ecker et al. . |
| 5,444,166 | 8/1995 | Ecker et al. . |
| 5,602,322 | 2/1997 | Ecker et al. . |
| 5,650,553 | 7/1997 | Ecker et al. . |
| 5,674,701 | 10/1997 | Ecker et al. . |

OTHER PUBLICATIONS

Nathan et al., Nitric Oxide as a Secretory Product of Mammalian Cells, The FASEB Journal, Sep. 1992, pp. 3051–3064, vol. 6.
Karupia et al., Inhibition of Viral Replication by Interferon-γ-Induced Nitric Oxide Synthase, Science, 10 Sep. 1993, pp. 1445–1448, vol. 261.
Nathan, et al., Natural Resistance and Nitric Oxide, Cell, Sep. 22, 1995, pp. 873–876, vol. 82.
Belouchi et al., Cloning and Characterization of the OsNramp Family from *Oryza Sativa,* a New Family of Membrane Proteins Possibly Implicated in the Transport of Metal Ions, Plant Molecular Biology, 1997, pp. 1085–1092, vol. 33, Kluwer Academic Publishers, Belgium.
Delledone et al., Nitric Oxide Functions as a Signal in Plant Disease Resistance, Nature, Aug. 1998, pp. 585–588, vol. 394.

Durner et al., Defense Gene Induction in Tobacco by Nitric Oxide, Cyclic GMP, and Cyclic ADP–Ribose, Proc. Natl. Acad. Sci. USA, Aug. 1998, pp. 10328–10333, vol. 95, USA.
Belouchi, A. et al., The Macrophage–Specific Membrane ProteinNramp Controlling Natural Resistance to Infections in Mice as Homologues Expressed in the Root System of Plants, Plant Molecular Biology, 1995, pp. 1181–1196, vol. 29.
Belouchi, A. et al., Cloning and Characterization of the OsNramp Family From *Oryza Sativa,* a New Family of Membrane Proteins Possibly Implicated in the Transport of Metal Ions, Plant Molecular Biology, 1997, pp. 1085–1092, vol. 33.
Cueto, M. et al., Presence of Nitric Oxide Synthase Activity in Roots and Nodules ofLupinus Albus, Febs. Letters, Dec. 2, 1996, pp. 159–164, vol. 398, No. 2–3.
Huang, J–S, et al., Involvement of Nitric Oxyde in Ralstonia Solanacearum–Induced Hypersensitive Reaction in Tobacco, Bacterial Wilt Disease: Molecular and Ecological Aspects, 1998, pp. 218–224.
Durner, J. et al., Defense Gene Induction in Tobacco by NitricOxyde, Cyclic GMP, and Cyclic ADP–Ribose, Proceeding of the National Academy of Sciences, USA, Aug. 1998, pp. 10328–10333, vol. 95.
Delledonne, M. et al., Nitric Oxyde Functions as a Signal in Plant Disease Resistance, Nature, Aug. 6, 1998, pp. 585–588, vol. 394.
Liu et al. Proc. Nat. Acad. Sci. 1994. vol. 91: 1888–1892.*
Xie et al. Science. 1992. vol. 256: 225–228. The nucleotide sequences of GenBank Accession number: M87039 is enclosed.*
Strittmatter et al. Bio/Technology. 1995. vol. 13: 1085–1089.*

* cited by examiner

*Primary Examiner*—Paula Hutzell
*Assistant Examiner*—Ousama Zaphmont
(74) *Attorney, Agent, or Firm*—Alston & Bird LLP

(57) ABSTRACT

Compositions and methods to aid in protecting the plant from invading pathogenic organisms are provided. The compositions of the invention comprise genes that influence the levels of nitric oxide in plant cells. Such genes include those encoding nitric oxide synthase (iNOS) as well as natural resistance-associated macrophage proteins (NRAMP) and NRAMP homologues. A pathogen inducible promoter or alternatively a constitutive, preferably a weak constitutive, promoter is used to control the desired level of disease control in the plant. Transformed plants, plant cells, tissues, and seed are also provided having enhanced disease resistance.

27 Claims, 2 Drawing Sheets

NITRIC OXIDE AS AN ACTIVATOR OF THE PLANT PATHOGEN DEFENSE SYSTEMS

CROSS-REFERENCE

This application claims the benefit of U.S. Provisional Application Ser. No. 60/076,153, filed Feb. 26, 1998.

FIELD OF THE INVENTION

The invention relates to the genetic manipulation of plants, particularly to transforming plants with genes that enhance disease resistance.

BACKGROUND OF THE INVENTION

Disease in plants is caused by biotic and abiotic causes. Biotic causes include fungi, viruses, bacteria, and nematodes. Of these, fungi are the most frequent causative agent of disease on plants. Abiotic causes of disease in plants include extremes of temperature, water, oxygen, soil pH, plus nutrient-element deficiencies and imbalances, excess heavy metals, and air pollution.

A host of cellular processes enables plants to defend themselves from disease caused by pathogenic agents. These processes apparently form an integrated set of resistance mechanisms that is activated by initial infection and then limits further spread of the invading pathogenic microorganism.

Subsequent to recognition of a potentially pathogenic microbe, plants can activate an array of biochemical responses. Generally, the plant responds by inducing several local responses in the cells immediately surrounding the infection site. The most common resistance response observed in both nonhost and race-specific interactions is termed the "hypersensitive response" (HR). In the hypersensitive response, cells contacted by the pathogen, and often neighboring cells, rapidly collapse and dry in a necrotic fleck. Other responses include the deposition of callose, the physical thickening of cell walls by lignification, and the synthesis of various antibiotic small molecules and proteins. Genetic factors in both the host and the pathogen determine the specificity of these local responses, which can be very effective in limiting the spread of infection.

As noted, among the causative agents of infectious disease of crop plants, the phytopathogenic fungi play the dominant role. Phytopathogenic fungi cause devastating epidemics, as well as causing significant annual crop yield losses. All of the approximately 300,000 species of flowering plants are attacked by pathogenic fungi. However, a single plant species can be host to only a few fungal species, and similarly, most fungi usually have a limited host range.

Plant disease outbreaks have resulted in catastrophic crop failures that have triggered famines and caused major social change. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight. Accordingly, molecular methods are needed to supplement traditional breeding methods to protect plants from pathogen attack.

SUMMARY OF THE INVENTION

Compositions and methods to aid in protecting a plant from invading pathogenic organisms are provided. The compositions of the invention comprise genes that influence the levels of nitric oxide in plant cells and regulate metal ion transport. Such genes include those encoding nitric oxide synthase (iNOS) as well as natural resistance-associated macrophage proteins (NRAMP) and NRAMP homologues. The compositions and methods of the invention can be used for enhancing resistance to plant pests. The method involves stably transforming a plant with a nucleotide sequence capable of altering the levels of nitric oxide in the plant cell, preferably increasing nitric oxide. The nucleotide sequences will be expressed from a promoter capable of driving expression of a gene in a plant cell. It is recognized that a variety of promoters will be useful in the invention the choice of which will depend in part upon the desired level of expression of the disclosed genes. It is recognized that the levels of expression can be controlled to provide a low level of nitric oxide in the plant to prevent pathogen invasion resulting in levels of immunity in the plant that impart pathogen resistance. Alternatively, the promoters can provide expression at levels to induce cell death. In these latter instances, it is recognized that pathogen inducible promoters will be utilized.

The methods of the invention find use in controlling plant pests, including fungal pathogens, viruses, nematodes, insects, and the like. Transformed plants and seeds, as well as methods for making such plants and seeds are additionally provided.

DETAILED DESCRIPTION OF THE INVENTION

Figure 1:
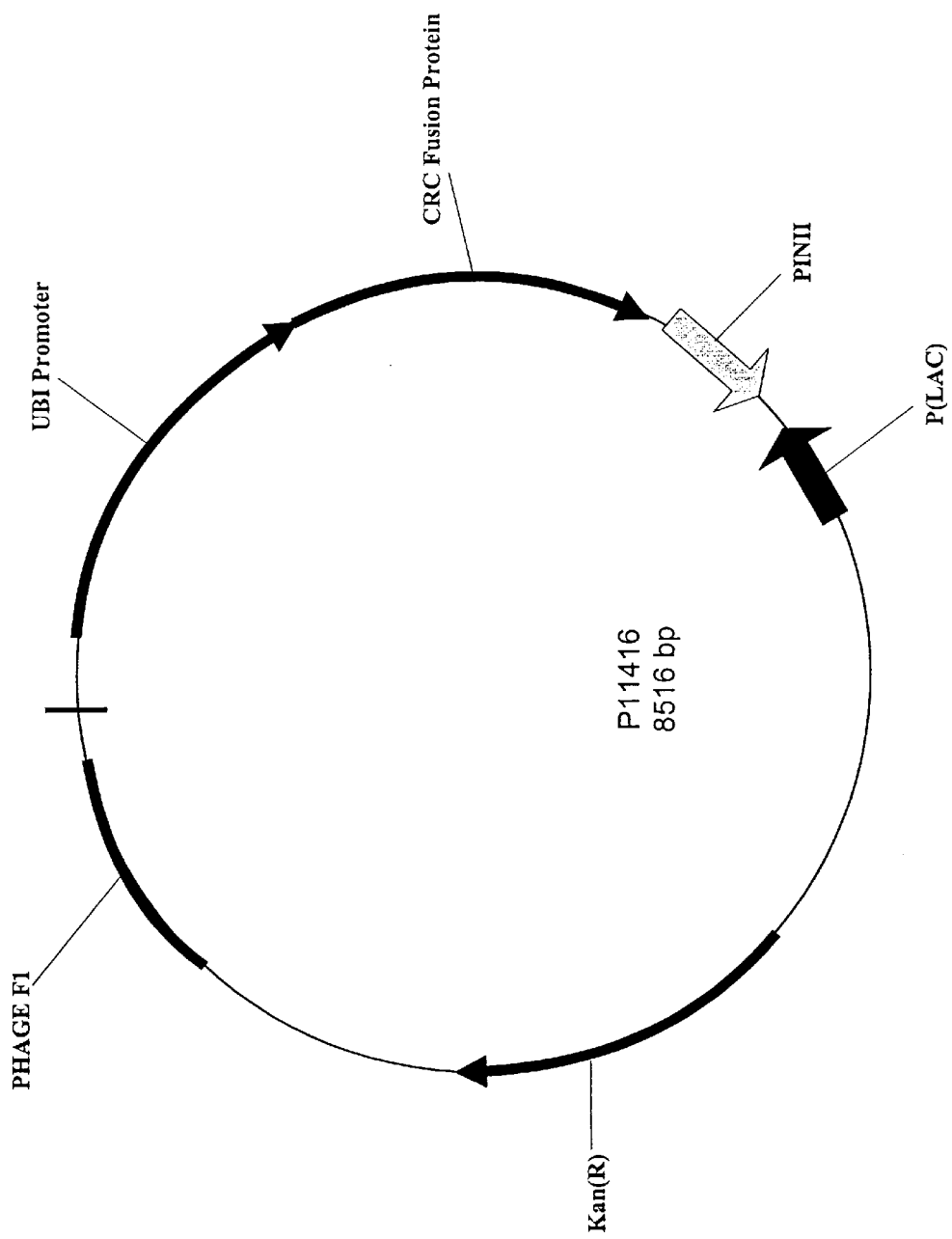
FIG. 1 schematically illustrates the plasmid construct comprising the ubiquitin promoter and CRC fusion protein gene.

The invention is drawn to methods for inducing resistance in a plant to plant pests by altering the levels of nitric oxide in the cell. Accordingly, the methods are also useful in protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms. The methods of the invention can be utilized to protect plants from disease, particularly those diseases that are caused by plant pathogens.

Pathogens of the invention include, but are not limited to, viruses or viroids, bacteria, insects, nematodes, fungi, and the like. Viruses include tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassuicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum,*

*Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassicola, Pythium ultimum, Peronospora parasitica, Fusarium roseum, Alternaria alternata*; Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora triticirepentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis* O, T *(Cochliobolus heterostrophus), Helminthosporium carbonum* I, II & III *(Cochliobolus carbonum), Exserohilum turcicum* I, II & III, *Helminthosporium pedicellatum, Physoderma maydis, Phyllosticta maydis, Kabatiella-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvulariapallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola (Glomerella graminicola), Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root knot, cyst and lesion nematodes, etc.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; Spodoptera frugiperda, fall armyworm; *Elasmopalpus lignosellus*, lesser cornstalk borer; *Agrotis orthogonia*, western cutworm; *Elasmopalpus lignosellus*, lesser cornstalk borer; Oulema melanopus, cereal leaf beetle; *Hypera punctata*, clover leaf weevil; *Diabrotica*

*undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; zygogramma exclamationis, sunflower beetle; *Bothyrus gibbosus*, carrot beetle; *Neolasioptera murtfeldtiana*, sunflower seed midge; Cotton: *Heliothis virescens*, cotton budworm; Helicoverpa zea, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae, rice weevil; Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescensl , cotton budworm; Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

The nucleotide sequences of the invention include those from plants as well as those of nonplant origin. NRAMP sequences have been isolated from bovine, ovine and avian sources, from *Drosophila melanogaster* (GenBank Accession No. U23948), *Caenorhabditis elegans* (Gen Bank U23525), yeast (Ecker J. R. (1996) *Proc. Natl. Acad. Sci. USA* 93:5624–28), *Mycobacterium leprae* (GenBank U 15184), *Oryza sativa* (GenBank D15268 and D25033, Belouchi et al. (1997) *Mol. Biol.* 33:1085–92), *Arabidopsis thaliana* (GenBank Z30530), all of which are herein incorporated by reference. NRAMP homologue sequences can be isolated from other sources including plant, i.e., maize, sources based on homology to known NRAMP sequences. Maize NRAMP homologue sequences are provided in SEQ ID NOs: 1, 2, 3, 4, 5, 6, 7, 8, and 9.

In particular, the present invention provides for isolated nucleic acid molecules comprising nucleotide sequences encoding the DNA sequence deposited in a bacterial host as ATCC Accession No. 207013. Further provided are polypeptides having an amino acid sequence encoded by a nucleic acid molecule described herein, for example those set forth in SEQ ID NOs: 1, 2, 3, 4, 5, 6, 7, 8, and 9, those deposited as ATCC Accession No. 207013, and fragments and variants thereof.

Plasmids containing the nucleotide sequences of the invention were deposited with American Type Culture Collection (ATCC), Manassas, Virginia, and assigned Accession No. 207013. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The invention encompasses isolated or substantially purified nucleic acid compositions. An "isolated" or "purified" nucleic acid molecule, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence, for example, control nitric oxide levels and regulate metal ion transport. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the entire nucleotide sequence encoding the proteins of the invention.

A fragment of an NRAMP nucleotide sequence that encodes a biologically active portion of an NRAMP protein of the invention will encode at least 15, 25, 30, 50, 100, 150, or 200 contiguous amino acids, or up to the total number of amino acids present in a full-length NRAMP protein of the invention. Fragments of an NRAMP nucleotide sequence that are useful as hybridization probes for PCR primers generally need not encode a biologically active portion of an NRAMP protein.

A fragment of an NRAMP nucleotide sequence may encode a biologically active portion of an NRAMP protein, or it may be a fragment that can be used as a hybridization probe or PCR primer using methods disclosed below. A biologically active portion of an NRAMP protein can be prepared by isolating a portion of one of the NRAMP nucleotide sequences of the invention, expressing the encoded portion of the NRAMP protein (e.g., by recombinant expression in vitro), and assessing the activity of the encoded portion of the NRAMP protein. Nucleic acid molecules that are fragments of an NRAMP nucleotide sequence comprise at least 15, 20, 50, 75, 100, 325, 350, 375, 400, 425, 450, 500, 550, 600, 650, 700, 800, 900, 1,000, 1,100, 1,200, 1,300, or 1,400 nucleotides, or up to the number of nucleotides present in a full-length NRAMP nucleotide sequence disclosed herein.

By "variants" is intended substantially similar sequences. For nucleotide sequences, conservative variants include those sequences that, because of the degeneracy of the genetic code, encode the amino acid sequence of one of the NRAMP proteins of the invention. Generally, nucleotide sequence variants of the invention will have at least 50%, 60%, to 70%, generally, 80%, preferably 85%, 90%, up to 98% sequence identity to its respective native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation.

The proteins of the invention may be altered in various ways including amino acid substitutions, deletions, truncations, and insertions. Methods for such manipulations are generally known in the art. For example, amino acid sequence variants of the proteins can be prepared by mutations in the DNA. Methods for mutagenesis and nucleotide sequence alterations are well known in the art. See, for example, Kunkel, T. (1985) *Proc. Natl. Acad. Sci. USA* 82:488–492; Kunkel et al. (1987) *Methods in Enzymol.* 154:367–382; U.S. Pat. No. 4,873,192; Walker et al. (1983) (eds.) *Techniques in Molecular Biology*, MacMillan Publishing Company, NY and the references cited therein. Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired defense activation activity. Obviously, the mutations that will be made in the DNA encoding the variant must not place the sequence out of reading frame and preferably will not create complementary regions that could produce secondary mRNA structure. See, EP Patent Application Publication No. 75,444.

The disclosed nucleotide sequences can be used to isolate other homologous sequences in other plant species. Methods are readily available in the art for the hybridization of nucleic acid sequences. Coding sequences from other plants may be isolated according to well known techniques based on their sequence homology to the coding sequences set forth herein. In these techniques all or part of the known coding sequence is used as a probe which selectively hybridizes to other NRAMP coding sequences present in a population of cloned genomic DNA fragments or cDNA fragments (i.e., genomic or cDNA libraries) from a chosen organism.

The genes of the invention include inducible nitric oxide synthase (iNOS) genes, natural resistance-associated macrophage proteins (NRAMP), and NRAMP homologues. Such genes are known in the art. See, for example, Xie et al. (1992) *Science* 256:225–228); Kinugawa et al. (1997) *Circ. Res.* 81(6):911–921; Kullo et al. (1997) *Circulation* 96(7): 2254–2261; Watkins et al. (1997) *Am. J. Respir. Cell Mol. Biol.* 16(6):629–639; Niwa et al. (1997) *Life Sci.* 61(5):PL. PMID: 9247328; UI: 97388494; Yuda et al. (1996) *Eur. J. Biochem* 242(3):807–812, PMID: 9022713; ui: 97175053; Beck et al. (1996) *FEBS Lett.* 394(3):263–267; Eberhardt et al. (1996) *Biochem. Biophys. Res. Commun.* 223(3): 752–756; Lin et al. (1996) *J Biol Chem.* 271(20): 11911–11919; Belouchi et al. (1997) *Plant Mol. Biol.* 33(6): 1085–1092; Belouchi et al. (1995) *Plant Mol. Biol.* 29(6): 1181–1196; Vidal et al. (1995) *J. Leukoc. Biol.* 58(4): 382–390; Kishi et al. (1995) *Immunol. Lett.* 47(1–2):93–96; Govoni et al. (1995) *Genomics* 27(1):9–19; Liu et al. (1995) *Am. J. Hum Genet.* 56(4):845–853; Vidal et al. (1995) *Mamm Genome* 6(4):224–230; Blackwell et al. (1995) *Mol Med.* 1(2):194–205; Pitel et al. (1994) *Mamm Genome.* 5(12):834–835; Cellier et al. (1994) *J. Exp. Med.* 180(5): 1741–1752; Govoni et al. (1995) *Genomics* 27(1):9–19; Hu et al. (1996) *DNA Cell Biol.* 15(2):113–123; Vidal et al. (1995) *Mamm Genome* 6(4):224–230; Blackwell et al. (1995) *Mol Med.* 1(2):194–205; Feng et al. (1996) *Genome Res.* 6(10):956–964; Govoni et al. (1997) *J. Leukoc. Biol.* 62(2):277–286; herein incorporated by reference.

To obtain other sequences, the entire NRAMP sequence or portions thereof may be used as probes capable of specifically hybridizing to corresponding coding sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify the NRAMP coding sequences of interest from a chosen organism by the well-known process of polymerase chain reaction (PCR). This technique may be used to isolate additional coding sequences from a desired organism or as a diagnostic assay to determine the presence of coding sequences in an organism.

Such techniques include hybridization screening of plated DNA libraries (either plaques or colonies; see, e.g. Sambrook et al. (1989) *Molecular Cloning. A Laboratory Manual* (2d ed., Cold Spring Harbor Laboratory Press, Plainview, N.Y.) and amplification by PCR using oligonucleotide primers corresponding to sequence domains conserved among the amino acid sequences (see, e.g. Innis et al., eds. (1990) *PCR Protocols, a Guide to Methods and Applications* (Academic Press, New York).

For example, hybridization of such sequences may be carried out under conditions of reduced stringency, medium stringency or even stringent conditions (e.g., conditions represented by a wash stringency of 35–40% Formamide with 5xDenhardt's solution, 0.5% SDS and 1xSSPE at 37° C.; conditions represented by a wash stringency of 40–45% Formamide with 5x Denhardt's solution, 0.5% SDS, and 1xSSPE at 42° C.; and conditions represented by a wash stringency of 50% Formamide with 5xDenhardt's solution, 0.5% SDS and 1xSSPE at 42° C., respectively), to DNA encoding the NRAMP genes disclosed herein in a standard hybridization assay. See Sambrook et al. (1989) Molecular Cloning. A Laboratory Manual (2d ed., Cold Spring Harbor Laboratory Press, Plainview, N.Y.). In general, sequences which code for an NRAMP homologue sequence and hybridize to the NRAMP sequences disclosed herein will be at least 62% homologous, 70%, 80%, 85%, 90%, 95% homologous, and even 98% homologous or more with the disclosed sequence. That is, the sequence similarity of sequences may range, sharing at least about 62%, about 70%, and even about 80%, 85%, 90%, 95%, 98% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length CDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith et al. (1981) Adv. Appl. Math. 2:482; by the homology alignment algorithm of Needleman et al. (1970) J. Mol. Biol. 48:443; by the search for similarity method of Pearson et al. (1988) Proc. Natl. Acad. Sci. 85:2444; by computerized implementations of these algorithms, including, but not limited to: CLUSTAL in the PC/Gene program by Intelligenetics, Mountain View, California; GAP, BESTFIT, BLAST, FASTA, and TFASTA in the Wisconsin Genetics Software Package, Genetics Computer Group (GCG), 575 Science Drive, Madison, Wis., USA; the CLUSTAL program is well described by Higgins et al. (1988) Gene 73:237–244 (1988); Higgins et al. (1989) CABIOS 5:151–153 ; Corpet et al. (1988) Nucleic Acids Research 16:10881–90; Huang et al. (1992) Computer Applications in the Biosciences 8:155–65, and Person et al. (1994) Methods of Molecular Biology 24:307–331; preferred computer alignment methods also include the BLASTP, BLASTN, and BLASTX algorithms (see Altschul et al. (1990) J. Mol. Biol. 215:403–410). Alignment is also often performed by inspection and manual alignment.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. to about 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent wash conditions are those in which the salt concentration is about 0.02 molar at pH 7 and the temperature is at least about 50, 55, or 60° C. However, nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) J. Mol. Biol. 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

While the invention is not bound by any particular mechanism of action, the gene products, probably proteins or polypeptides, function to activate the formation of nitric oxide and ultimately to activate the defense system. Nitric oxide is directly toxic to pathogens and thus functions to avoid pathogen invasion. Secondly, nitric oxide reactive oxygen species induce the defense system and disease resistance in plants. Thus, nitric oxide can interact with other compounds to produce secondary reactive oxygen species. Nitric oxide promotes a strong hypersensitive disease- resistance response. The activation of the defense system may involve inducing resistance of the plant to pathogen invasion. Thus, the transformed plant has an elevated disease resistance or immunity to pathogens. Alternatively, nitric oxide can function as a nonspecific general toxin and work against any pathogen.

The activation of the plant defense system may involve the induced production of gene products, such as PR proteins and various secondary metabolites, many of which are antipathogenic. The induction may involve inducing the accumulation of cytotoxic phytoalexins and the deposition of callose and lignin in cell walls. Likewise, the induction may involve the activation of transcription factors, reactive oxygen species, ion fluxes, G proteins, salicylic acids and other HR and plant defense regulators. It is recognized that the present invention is not dependent upon a particular mechanism of defense. Rather, the genes and methods of the invention work to increase resistance of the plant to pathogens independent of how that resistance is brought.

The NRAMP genes and proteins as well as the NRAMP homologue genes and proteins of the invention can also be used to control resistance to pathogens by altering nitric oxide levels. While the exact function of the NRAMP homologues is not known, they are involved in controlling nitric oxide levels, in transporting of metal ions, and potentially influencing the expression of defense-related proteins. It is recognized that the present invention is not premised upon any particular mechanism of action of the NRAMP genes. It is sufficient for purposes of the invention that the genes and proteins are involved in the plant defense system and can be used to increase resistance levels in the plant to pathogens.

The NRAMP genes and proteins belong to a highly conserved NRAMP gene family. The genes display similarity even between plant and mammalian sequences. The genes contain transmembrane (TM) domains, glycosylation signals, and transport signatures. The degree of structural similarity between the plant and mammalian genes indicates that the plant genes are involved in metal ion transport.

Likewise, the invention encompasses iNOS genes and proteins and their use. Nitric oxide synthase produces large amounts of the radical gas, nitric oxide (NO), from a guanidino nitrogen of L-arginine. Expression of iNOS in a plant cell defends the cells against pathogens.

The present invention also encompasses nucleotide sequences encoding the nitric-oxide-producing genes and proteins as well as components and fragments thereof. That is, it is recognized that component polypeptides or fragments of the proteins may be produced that retain iNOS and NRAMP activity. These fragments include truncated sequences, as well as N-terminal, C-terminal, internal and internally deleted amino acid sequences of the proteins.

Most deletions, insertions, and substitutions of the protein sequence are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by the induction of the plant defense system. See, for example U.S. Pat. No. 5,614,395, herein incorporated by reference.

The plant defense mechanisms described herein may be used alone or in combination with other proteins or agents to protect against plant diseases and pathogens. Other plant defense proteins include those described in copending applications entitled "Methods for Enhancing Disease Resistance in Plants", U.S. application Ser. No. 60/076,151, filed Feb. 26, 1998, and U.S. application Ser. No. 60/092,464, filed Jul. 11, 1998, and copending application entitled "Genes for Activation of Plant Pathogen Defense Systems", U.S. application Ser. No. 60/076,083, filed Feb. 26, 1998, all of which are herein incorporated by reference.

As discussed, the expression of the iNOS and NRAMP nucleotides in the plant cell induces the disease resistance pathway or induces immunity, i.e., disease resistance, in the plant. That is, the expression of the genes can induce a defense response in the cell or alternatively can cause cell death. The end result can be controlled by the level of expression of the sequences in the plant.

A number of promoters can be used in the practice of the invention. The promoters can be selected based on the desired outcome. When the genes are expressed at levels to causes cell death, an inducible promoter can be used to drive the expression of the genes of the invention. The inducible promoter must be tightly regulated to prevent unnecessary cell death yet be expressed in the presence of a pathogen to prevent infection and disease symptoms. Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See, also the copending applications entitled "Inducible Maize Promoters", U.S. application Ser. No. 60/076,100, filed Feb. 26, 1998 and U.S. application Ser. No. 60/079,648, filed Feb. 27, 1998, and herein incorporated by reference.

Of interest are promoters that are expressed locally at or near the site of pathogen infection. See, for example, Marineau et al. (1987) *Plant Mol. Biol.* 1:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Molecular and General Genetics* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; and the references cited therein. Of particular interest is the inducible promoter for the maize PRms gene, whose expression is induced by the pathogen Fusarium moniliforme (see, for example, Cordero et al. (1992) *Physiological and Molecular Plant Pathology* 41:189–200).

Additionally, as pathogens find entry into plants through wounds or insect damage, a wound inducible promoter may be used in the constructions of the invention. Such wound inducible promoters include potato proteinase inhibitor (pin II) gene (Ryan, *Ann. Rev. Phytopath.* 28:425–449; Duan et a., *Nature Biotechnology* 14:494–498); wun1 and wun2, U.S. Pat. No. 5,428,148; win1 and win2 (Stanford et al. Mol Gen Genet 215:200–208); systemin (McGurl et al. *Science* 225:1570–1573); WIP1 (Rohmeier et al. *Plant Mol Biol* 22:783–792; Eckelkamp et al. *FEBS Letters* 323:73–76); MPI gene (Corderok et al. *Plant Journal* 6(2): 141–150); and the like, herein incorporated by reference.

Where a low level expression of the nucleotide sequences is desired, weak promoters will be used. It is recognized that weak inducible promoters may be used. Additionally, either a weak constitutive or a weak tissue-specific promoter may be used. Such weak promoters cause activation of the plant defense system short of cell death. Thus, there is an activation of the plant defense system at levels sufficient to protect from pathogen invasion. In this state, there is at least a partial activation of the plant defense system wherein the plant produces increased levels of antipathogenic factors such as PR proteins, i.e., PR1, chitinases, β-glucanases, etc.; secondary metabolites; phytoalexins; reactive oxygen species; and the like.

Generally, by "weak promoter" is intended a promoter that drives expression of a coding sequence at a low level. By "low level" is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Such weak constitutive promoters include, for example, the core promoter of the Rsyn7 (copending U.S. application Ser. No. 08/661,601), the core 35S CaMV promoter, and the like. Other constitutive promoters include, for example, U.S. Pat. Nos. 5,608,149; 5,608,144; 5,604, 121; 5,569,597; 5,466,785; 5,399,680; 5,268,463; 5,608, 142. See also, copending application entitled "Constitutive Maize Promoters", U.S. application Ser. No. 60/076,075, filed Feb. 26, 1998, and herein incorporated by reference.

Tissue-specific promoters include Yamamoto et al. (1997) *Plant J.* 12(2)255–265; Kawamata et al. (1997) *Plant Cell Physiol.* 38(7):792–803; Hansen et al. (1997) *Mol Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl Cell Differ.* 20:181–196; Orozco et al. (1993) *Plant Mol Biol.* 23(6): 1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

The nucleotide sequences of the invention can be introduced into any plant. The genes to be introduced can be conveniently used in expression cassettes for introduction and expression in any plant of interest.

Such expression cassettes will comprise a transcriptional initiation region linked to the nucleotide sequence of interest. Such an expression cassette is provided with a plurality of restriction sites for insertion of the gene of interest to be under the transcriptional regulation of the regulatory regions. The expression cassette may additionally contain selectable marker genes.

The transcriptional initiation region, the promoter, may be native or analogous or foreign or heterologous to the plant host. Additionally, the promoter may be the natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nuc. Acids Res.* 17:7891–7903; Joshi et al. (1987) *Nuc. Acid Res.* 15:9627–9639.

The genes of the invention are provided in expression cassettes for expression in the plant of interest. The cassette will include 5' and 3' regulatory sequences operably linked to the gene of interest. The cassette may additionally contain at least one additional gene to be cotransformed into the organism. Alternatively, the additional gene(s) can be provided on another expression cassette. Where appropriate, the gene(s) may be optimized for increased expression in the transformed plant. That is, the genes can be synthesized using plant preferred codons for improved expression. Methods are available in the art for synthesizing plant preferred genes. See, for example, U.S. Pat. Nos. 5,380,831, 5,436,391, and Murray et al. (1989) *Nuc. Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, O. et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94; untranslated leader from the coat protein mRNA of alfalfa mosaic virus (AMV RNA 4), (Jobling et al. (1987) *Nature* 325:622–625; tobacco mosaic virus leader (TMV), (Gallie, D. R. (1989) *Molecular Biology of RNA* 237–256; and maize chlorotic mottle virus leader (MCMV) (Lommel et al. (1991) *Virology* 81:382–385). See also, Della-Cioppa et al. (1987) *Plant Physiology* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions, may be involved.

The genes of the present invention can be used to transform any plant. In this manner, genetically modified plants, plant cells, plant tissue, seed, and the like can be obtained. Transformation protocols may vary depending on the type of plant or plant cell, i.e., monocot or dicot, targeted for transformation. Suitable methods of transforming plant cells include microinjection (Crossway et al. (1986) Biotechniques 4:320–334), electroporation (Riggs et al. (1986) Proc. Natl. Acad Sci. USA 83:5602–5606, Agrobacterium mediated transformation (Hinchee et al (1988) Biotechnology 6:915–921), direct gene transfer (Paszkowski et al. (1984) EMBO J 3:2717–2722), and ballistic particle acceleration (see, for example, Sanford et al, U.S. Pat. 4,945,050; Tomes et al. "Direct DNA Transfer into Intact Plant Cells via Microprojectile Bombardment" In Gamborg and Phillips (Eds.) Plant Cell, Tissue and Organ Culture: Fundamental Methods, Springer-Verlag, Berlin (1995); and McCabe et al. (1988) Biotechnology 6:923–926). Also see, Weissinger et al. (1988) Annual Rev. Genet. 22:421–477; Sanford et al (1987) Particulate Science and Technology 5:27–37 (onion); Christou et al. (1988) Plant Physiol. 87:671–674(soybean); McCabe et al (1988) Bio/Technology 6:923–926 (soybean); Datta et al (1990) Biotechnology 8:736–740 (rice); Klein et al. (1988) Proc. Natl. Acad Sci. USA 5:4305–4309 (maize); Klein et al. (1988) Biotechnology 6:559–563 (maize); Tomes et al. "Direct DNA Transfer into Intact Plant Cells via Microprojectile Bombardment" In Gamborg and Phillips (eds.) Plant Cell, Tissue and Organ Culture: Fundamental Methods, Springer-Verlag, Berlin (1995) (maize); Klein et al. (1988) Plant Physiol. 91:440–444(maize); Fromm et al. (1990) Biotechnology 8:833–839 (maize); Hooydaas-Van Slogteren et al. (1984) Nature (London) 311:763–764; Bytebier et al. (1987) Proc. Natl. Acad. Sci. USA 84:5345–5349 (Liliaceae); De Wet et al. (1985) In The Experimental Manipulation of Ovule Tissues ed. G. P. Chapman et al., pp. 197–209. Longman, N.Y. (pollen); Kaeppler et al. (1990) Plant Cell Reports 9:415–418; and Kaeppler et al. (1992) Theor. Appl. Genet. 84:560–566 (whisker-mediated transformation); D'Halluin et al. (1992) Plant Cell 4:1495-1505 (electroporation); Li et al. (1993) Plant Cell Reports 12:250–255 and Christou and Ford (1995) Annals of Botany 75:407–413 (rice); Osjoda et al. (1996) Nature Biotechnology 14:745–750 (maize via Agrobacterium tumefaciens); all of which are herein incorporated by reference.

The cells which have been transformed may be grown into plants in accordance with conventional ways. See, for example, McCormick et al. (1986) Plant Cell Reports 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The methods of the invention can be used with other methods available in the art for enhancing disease resistance in plants.

The following examples are offered by way of illustration and not by way of limitation.

EXPERIMENTAL

EXAMPLE 1

Disease Resistant Transient Gene Expression Assay Using Biolistics Particle Bombardment A transient gene expression assay, as modified from Nelson et al. (1997) Transgenic Res. 6:233–244), was used to evaluate the ability of an introduced iNOS gene to activate the plant defense system. The gene is the clone for a mouse iNOS. The sequence of the iNOS gene is set forth in Xie et al. (1992) Science 256:225–228, herein incorporated by reference. In the method, a particle bombardment system is used to simultaneously introduce a construct comprising a reporter gene driven by a constitutive promoter and a construct comprising the iNOS gene with its promoter into maize cells for the purposes of studying physiological processes, foremost amongst them the plant defense response.

In this example, the first construct comprises a ubiquitin promoter driving the expression of the reporter CRC fusion protein gene, which when expressed causes cells to turn red due to anthocyanin production. Other reporter genes, such as GUS, luciferase, or green fluorescent protein, can be used in this assay. The second construct comprises the iNOS sequence driven by the constitutive Rsyn7 promoter. Following cobombardment of cells with these constructs, expression of the iNOS genes within a cell causes a hypersensitive-type disease response involving cell death, or at the very least radically redirected gene expression. Such cell death disrupts the expression of the reporter gene, such that the occurrence of visible, anthocyanin-containing phenotypes is suppressed in these cobombardment experiments.

Tissue Sources

Experiments were performed with immature embryos, essentially the scutellar surface. Mature embryos from germinated seeds have also been used with similar results.

Immature Embryos

Immature embryos from an inbred line were isolated from ears 9-11 days after pollination using a scalpel. Prior to embryo isolation, pollinated ears were surface-sterilized with a microdetergent and 25% commercial bleach mixture, then washed with 3 exchanges of sterile $H_2O$. Two hundred embryos, approximately 1.5–1.8 mm long, are placed on a high sucrose culture medium six hours prior to bombardment and then aligned in a target grid about 1.4 cm wide.

DNA Sources

The DNA constructs of interest used in this example included: plasmid p11416 (FIG. 1), comprising the ubiquitin promoter (ubi) and the CRC fusion protein gene (ubi: :CRC fusion), the expression of which yields the anthocyanin-producing, or red cell, phenotype; and a plasmid comprising the Rsyn7 promoter (WO 97/47756, herein incorporated by reference) and the iNOS gene (Rsyn7::iNOS) (FIG. 2), the expression of which yields the iNOS product.

Plasmid p7770 (not shown), comprising an empty Rsyn7 promoter construct (Rsyn7::pinII terminator), was used as a control to balance promoter site molarity;

and plasmid p7731 (not shown), an inert DNA filler, was used to balance the amount of DNA shot with each bombardment episode.

Embryos and leaf tissue were transformed by the tungsten particle biolistic method (Tomes et al. (1995) supra; Koziel et al. (1993) Bio/Technology 11:194–200) using a high pressure particle delivery system (Biolistic Particle Delivery System Model PDS-100 by DuPont). Forty-five embryos, arranged in 5 plates, each with 9 embryos, were subjected to bombardment with the ubi: :CRC fusion onstruct alone (Treatment A) or to cobombardment with the ubi::CRC fusion construct and the Rsyn7::iNOS construct (Treatment B). Following bombardment, embryos were stored in the dark for 36 hours at 23° C.

Quantification and Verification of Gene Expression

Expression of the CRC fusion gene is quantified by visual means 16 to 48 hours, more usually 36 hours, following bombardment. Cells expressing the CRC fusion protein gene were red in color.

Activation of the defense system, using the maize PRI protein as a marker, is verified with an antibody Western blot for the PR-1 class of pathogenesis-related proteins. Forty-eight hours after bombardment, 18 embryos for each treatment are pooled and their protein extracted and run on SDS-PAGE, electroblotted onto 0.2 micron PVDV membrane, and probed with antibodies raised against tobacco PR-1 protein.

Results

A 3-fold suppression of CRC reporter gene expression was observed utilizing the iNOS cDNA (Table 1). The results indicate that iNOS represses CRC expression, indicating a possible activation of the plant pathogen defense system. This data indicates that the iNOS gene is acting as a defense activator in maize.

TABLE 1

Expression of CRC anthocyanin reporter gene system in particle-bombarded maize tissues with or without cobombardment with the mouse iNOS gene in the Rsyn7-iNOS Construct (P7821).

| Maize Variety | Tissue[1] | CRC Control Ave[3] | SE[3] | CRC + iNOS Ave[3] | SE[3] | Ratio[2] |
|---|---|---|---|---|---|---|
| HG11 | ME | 24.8 | 4.8 | 8.0 | 18.0 | 3.1 |
| A63 | LF | 3.5 | 1.4 | 2.2 | 1.2 | 1.6 |
| A63 | LF[4] | 137.4 | 36.0 | 84.0 | 18.4 | 1.6 |

[1]Tissues are: ME, mature embryo; and LF, leaf.
[2]Ratio of average number of red transformed spots (cells) for CRC control over average number for CRC + iNOS.
[3]Averages and standard errors from N = 4 separate bombardments for mature embryos, N = 5 for immature embryos, and between N = 10 for leaves.
[4]Leaf tissue bombardments used for PR westerns.

EXAMPLE 2

Disease Resistant Transient Gene Expression Assay Using Biolistics Particle Bombardment Following the methods outlined above, maize cells/callus were cobombarded with the same Rsyn7-iNOS construct described above and with a ubiquitin promoter-luciferase reporter gene construct (not shown). Cobombardment with the Rsyn7-iNOS construct caused a suppression of luciferase expression (Table 2).

TABLE 2

Expression of ubiquitin-luciferase reporter gene system in particle-bombarded maize tissue with or without cobombardment with the mouse iNOS gene in the Rsyn7-iNOS Construct (P7821).

| Maize Variety | Tissue[1] | Luc Control Ave[3] | SE[3] | Luc + iNOS Ave[3] | SE[3] | Ratio[2] |
|---|---|---|---|---|---|---|
| HG11 | Callus | 1813 | 401 | 721 | 229 | 2.51 |

[1]Tissue was cells or callus.
[2]Ratio of average luciferase units/microgram of total protein in the extract in the luciferase only control over the average luciferase units/microgram in the cobombardment of luciferase plus iNOS.
[3]Averages and SE derived from N = 2 for the control, and N = 3 for the iNOS cobombardment.

This luciferase reporter gene experiment is consistent with the results generated using the CRC reporter gene system. Moreover, by demonstrating the effect in yet a third tissue, it further indicates that the suppression effect by iNOS is real.

The suppression of CRC reporter gene expression by cobombardment with the Rsyn7-iNOS construct indicates that the iNOS gene expression is having an effect on the plant cells' physiology. As activation of the defense system involves programmed cell death and/or radical alteration of gene expression, this suppression is consistent with activation of a defense system. This suppression was observed in both bombarded leaf tissue and mature embryos. The PR1 protein expression is a commonly used indicator of plant defense system activation. The bombardment data indicate that the iNOS gene is operating as an activator of plant defense systems in plants, as seen by the results in maize.

The means by which the iNOS expression is activating defense is presumably through the production of nitric oxide. Nitric oxide is a highly reactive chemical species, and it is likely that it is either directly, or indirectly through other reactive oxygen species, acting as a signal to turn on the plant defense system. Plant defense systems are well known to be activated by reactive chemical, and in particular reactive oxygen stress.

EXAMPLE 3

Transformation and Regeneration of Transgenic Plants

Figure 2:
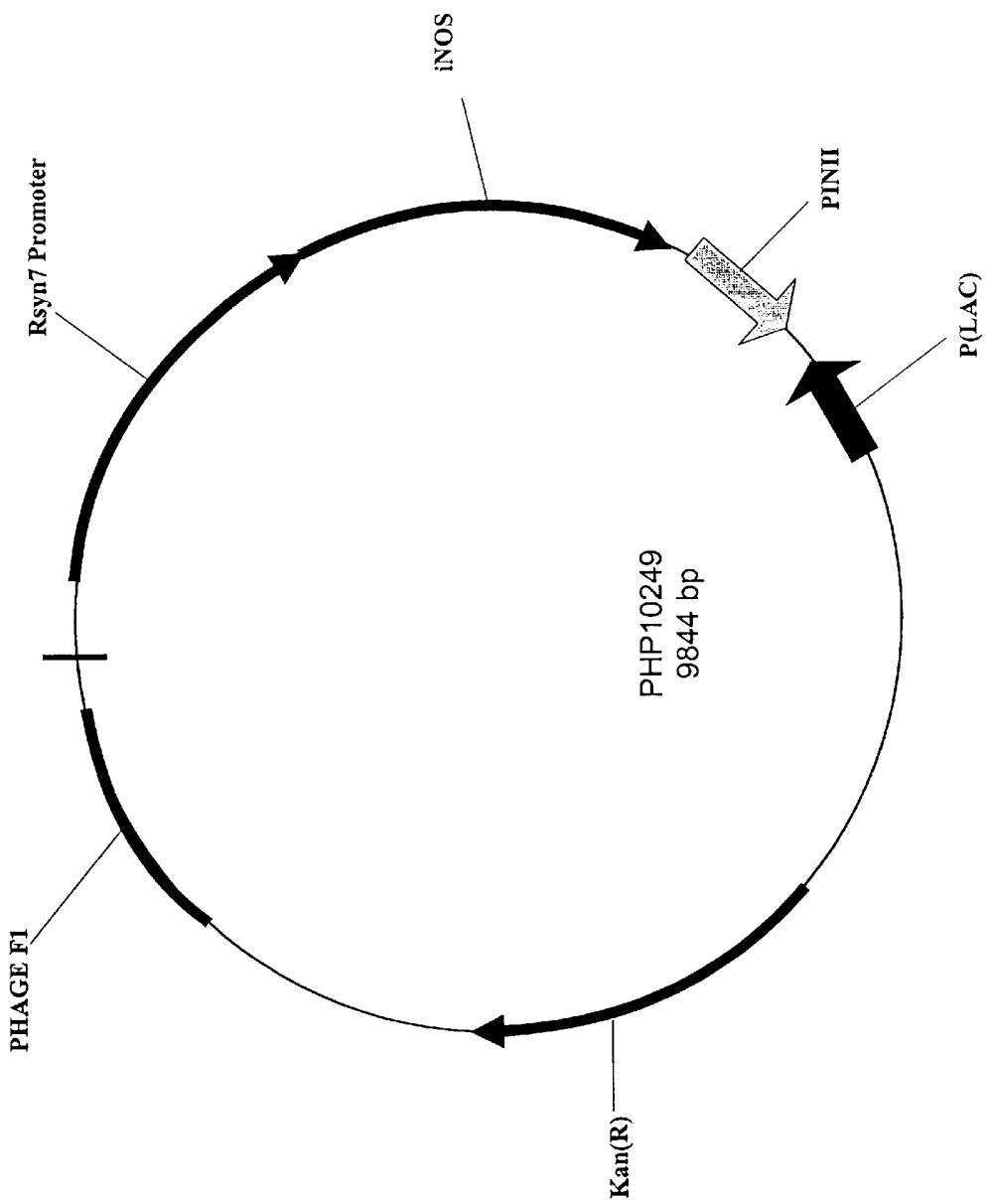
FIG. 2 schematically illustrates the plasmid construct comprising the Rsyn7 promoter and an iNOS gene.

An NRAMP nucleotide sequence of the invention is cloned into a plant expression vector as shown in FIG. 1 in place of the CRC fusion gene. The nucleotide sequence is under transcriptional control of the maize ubiquitin promoter. A selectable marker, the PAT gene, is used.

Immature maize embryos from greenhouse donor plants are bombarded with a plasmid containing the NRAMP sequence operably linked to the ubiquitin promoter plus a plasmid containing the selectable marker gene PAT (Wohlleben et al. (1988) *Gene* 70:25–37) that confers resistance to the herbicide Bialaphos. Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the NRAMP nucleotide sequence operably linked to the ubiquitin promoter is made. This plasmid DNA plus plasmid DNA containing a PAT selectable marker is precipitated onto 1.1 $\mu$m (average diameter) tungsten pellets using a $CaCl_2$ precipitation procedure as follows:

100 $\mu$l prepared tungsten particles in water
10 $\mu$l (1 $\mu$g) DNA in TrisEDTA buffer (1 $\mu$g total)
100 $\mu$l 2.5 M $CaCl_2$
10 $\mu$l 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 $\mu$l 100% ethanol is added to the final tungsten particle pellet. For particle gun bombardment, the tungsten/DNA particles are briefly sonicated and 10 $\mu$l spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for enhanced disease resistance.

APPENDIX

272 V

| Ingredient | Amount | Unit |
| --- | --- | --- |
| D-I $H_2O$ | 950.000 | ml |
| MS Salts (GIBCO 11117-074) | 4.300 | g |
| Myo-Inositol | 0.100 | g |
| MS Vitamins Stock Solution ## | 5.000 | ml |
| Sucrose | 40.000 | g |
| Bacto-Agar @ | 6.000 | g |

Directions:
@ = Add after bringing up to volume
Dissolve ingredients in polished D-I $H_2O$ in sequence
Adjust to pH 5.6
Bring up to volume with polished D-I $H_2O$ after adjusting pH
Sterilize and cool to 60° C.
## = Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.
Total Volume (L) = 1.00

288 J

| Ingredient | Amount | Unit |
| --- | --- | --- |
| D-I $H_2O$ | 950.000 | ml |
| MS Salts | 4.300 | g |
| Myo-Inositol | 0.100 | g |
| MS Vitamins Stock Solution ## | 5.000 | ml |
| Zeatin .5 mg/ml | 1.000 | ml |
| Sucrose | 60.000 | g |
| Gelrite @ | 3.000 | g |
| Indoleacetic Acid 0.5 mg/ml # | 2.000 | ml |
| .1 mM Abscisic Acid | 1.000 | ml |
| Bialaphos 1 mg/ml # | 3.000 | ml |

Directions:
@ = Add after bringing up to volume
Dissolve ingredients in polished D-I $H_2O$ in sequence
Adjust to pH 5.6
Bring up to volume with polished D-I $H_2O$ after adjusting pH
Sterilize and cool to 60° C.
Add 3.5 g/L of Gelrite for cell biology.
## = Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.
Total Volume (L) = 1.00

560 R

| Ingredient | Amount | Unit |
| --- | --- | --- |
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4 mg/ml | 1.250 | ml |
| Sucrose | 30.000 | g |
| 2,4-D 0.5 mg/ml | 4.000 | ml |
| Gelrite @ | 3.000 | g |
| Silver Nitrate 2 mg/ml # | 0.425 | ml |
| Bialaphos 1 mg/ml # | 3.000 | ml |

Directions:
@ = Add after bringing up to volume
# = Add after sterilizing and cooling to temp.
Dissolve ingredients in D-I $H_2O$ in sequence
Adjust to pH 5.8 with KOH
Bring up to volume with D-I $H_2O$
Sterilize and cool to room temp.
Total Volume (L) = 1.00

560 Y

| Ingredient | Amount | Unit |
| --- | --- | --- |
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4 mg/ml | 1.250 | ml |
| Sucrose | 120.000 | g |
| 2,4-D 0.5 mg/ml | 2.000 | ml |
| L-Proline | 2.880 | g |
| Gelrite # | 2.000 | g |
| Silver Nitrate 2mg/ml # | 4.250 | ml |

Directions:
@ = Add after bringing up to volume
# = Add after sterilizing and cooling to temp.
Dissolve ingredients in D-I $H_2O$ in sequence
Adjust to pH 5.8 with KOH
Bring up to volume with D-I $H_2O$
Sterilize and cool to room temp.
 Autoclave less time because of increased sucrose
Total Volume (L) = 1.00

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for increasing nitric oxide levels in a plant, said method comprising transforming said plant with a DNA construct comprising a nucleotide sequence capable of increasing the levels of nitric oxide in the plant cell operably linked to a promoter that drives expression of a coding sequence in a plant cell and regenerating stably transformed plants wherein said nucleotide sequence encodes a mouse nitric oxide synthase.

2. The method of claim 1, wherein said plant is a monocot.

3. The method of claim 2, wherein said monocot is maize.

4. The method of claim 2, wherein said promoter is a constitutive promoter.

5. The method of claim 4, wherein said constitutive promoter is selected from the group consisting of the core promoter of Rsyn7 promoter and the core promoter of 35S CaMV promoter.

6. The method of claim 1, wherein said promoter is an inducible promoter.

7. The method of claim 6, wherein said promoter is selected from the group consisting of a promoter for a maize PR-1 gene and a promoter for the maize PRms gene.

8. The method of claim 7, wherein said promoter is the promoter for the maize PRms gene.

9. A plant having stably incorporated into its genome a nucleotide sequence capable of increasing the levels of nitric oxide in a plant cell operably linked to a promoter that drives expression of a coding sequence in a plant cell; wherein said nucteotide sequence encodes a mouse nitric oxide synthase.

10. The plant of claim 9, wherein said plant is a monocot.

11. The plant of claim 10, wherein said monocot is maize.

12. The plant of claim 9, wherein said promoter is a constitutive promoter.

13. The plant of claim 12, wherein said constitutive promoter is selected from the group consisting of the core promoter of Rsyn7 promoter and the core promoter of 35S CaMV promoter.

14. The plant of claim 9, wherein said promoter is an inducible promoter.

15. The plant of claim 14, wherein said promoter is selected from the group consisting of a promoter for a maize PR-1 gene and a promoter for the maize PRms gene.

16. The plant of claim 15, wherein said promoter is the promoter for the maize PRms gene.

17. Seed of the plant of claim 9.

18. Seed of the plant of claim 10.

19. Seed of the plant of claim 11.

20. A plant cell having stably incorporated into its genome a nucleotide sequence capable of increasing the levels of nitric oxide in a plant cell operably linked to a promoter that drives expression of a coding sequence in a plant cell; wherein said nucleotide sequence encodes a mouse nitric oxide synthase.

21. The plant cell of claim 20, wherein said plant cell is a monocot.

22. The plant cell of claim 21, wherein said monocot is maize.

23. The plant cell of claim 20, wherein said promoter is a constitutive promoter.

24. The plant cell of claim 23, wherein said constitutive promoter is selected from the group consisting of the core promoter of Rsyn7 promoter and the core promoter of 35S CaMV promoter.

25. The plant cell of claim 20, wherein said promoter is an inducible promoter.

26. The plant cell of claim 25, wherein said promoter is selected from the group consisting of a promoter for a maize PR-1 gene and a promoter for the PRms maize gene.

27. The plant cell of claim 26, wherein said promoter is the promoter for the maize PRms gene.

* * * * *

UNITED STATES PATENT AND TRADEMARK OFFICE
CERTIFICATE OF CORRECTION

PATENT NO.    : 6,198,020 B1
DATED         : March 6, 2001
INVENTOR(S)   : Bowen et al.

Page 1 of 1

It is certified that error appears in the above-identified patent and that said Letters Patent is hereby corrected as shown below:

In the Assistant Examiner's name "Zaphmont" should read -- Zaghmount --.

Column 33,
Claim 4,
Line 19, "claim 2" should read -- claim 1 --.

Claim 9,
Line 37, "nucteotide" should read -- nucleotide --.

Signed and Sealed this

Twenty-eighth Day of August, 2001

*Attest:*

*Attesting Officer*

NICHOLAS P. GODICI
*Acting Director of the United States Patent and Trademark Office*

SEQUENCE LISTING

<160> NUMBER OF SEQ ID NOS: 9

<210> SEQ ID NO 1
<211> LENGTH: 1477
<212> TYPE: DNA
<213> ORGANISM: Zea mays
<220> FEATURE:
<223> OTHER INFORMATION: sequence gap between 488 and 489
<220> FEATURE:
<221> NAME/KEY: unsure
<222> LOCATION: (545)
<223> OTHER INFORMATION: Nucleotide at this position may be a or g or c or t.

<400> SEQUENCE: 1

```
atggcgtcga gcgacctcgc cgagagcctc ctccccggcg gcggggcgg agcctccgcc      60
tcacatgacg aatacgagga gcgcgcgtac gattccgagg acaagatctc catcgccgtc     120
tcggattccg acggcgaaga cgacggcacg ccggcgtcgc gcccgcccctt ctcgtggcgg    180
aagctctggc gcttcacggg cccgggtttt ctcatgtgca tcgcgttcct ggacccgggc    240
aatctggagg gggacctaca ggcgggcgcc gcggcggggt accagctgct gtggctgctc    300
ttgtgggcga cgatcatggg cgcgctgatg cagctgctct ccgcccggct cggcgtggcc    360
acagggaagc acctcgccga gctctgccgc caggagtacc ctccctgggc tactcgcgcg    420
ctctgggcca tgacggagct cgcgctcgtc ggcgcagaca tacaggaggt gattggcagc    480
gcgattgctt ttgccaaagg attttatgg tctaaacagg ctgacagtat aggtcttgag    540
aatgntgggc agtacttaca agaaaaatat ggaactgcat tctttcctat cctctatatc    600
tgggctgttg gtttgttagc atctgggcag agtagcacaa ttactggcac atatgcagga    660
cagtttgtta tgggaggttt ccttaatctt cgattgaaga agtggctacg agcaatgatt    720
actcgaagtt ttgccattat tccaactatg attgtggctt tattttcga tactcaagat    780
cctactatgg atattctgaa tgaagcactc aatgttcttc aatccataca gattccgttt    840
gctctaattc ctctcatcac cctcgtttca atgagcaaa tcatggggtc gttcgtaatt    900
ggtcccatca ccaaagtgat tagctggatt gttacggtat ttctgatgct tatcaacggg    960
tatcttatac tgtctttcta cattactgat gtccggggtg cattgcttcg ctcaagcttg   1020
tgtgttgtgt tggttgtcta ccttgcattc atcgtctatc ttattgtgcg aaatacttcg   1080
ctgtattctc gcctttgctc atcaacgtca aagagctcgt gagcgtttca acatcgtcat   1140
ctgctgcttt gatggactgg aacagtgctg tccatccatg caaagcttgt gctgctgctt   1200
atttattggc ttcacagaag actatgtatg catatcccgt gtatgcttgt gtttatggga   1260
tatttgatag tagggcttct tcccttttag gatgctatat tcacctccag gcacacgttg   1320
cagatagatt tcttatttct gaggtttatg gtgatgtgaa aagactactg gcaaaaaaaa   1380
actggcattg ctgttcctcc tgaaactgag cagatgaaat ttactgaatg atctgtaaag   1440
ctcgatgttg magttctgaa aaaaaaaaaa aaaaaaa                             1477
```

<210> SEQ ID NO 2
<211> LENGTH: 453
<212> TYPE: DNA
<213> ORGANISM: Zea mays

-continued

```
<400> SEQUENCE: 2
ggatttctcg tctcaattgc atatattgat cctggaaact ttgagacgga tctacaggct      60
ggagcacagt acaaatatga gcttctttgg atcatacttg ttgcatcctg tgctgctctt     120
attattcaat cacttgcagc caggctaggg gttgtgacag ggaaacatct tgcagagcat     180
tgcagggctg agtatcccaa ggtcacaaat tttgtcttat ggattcttgc agaacttgct     240
gttgttgcat gtgacattcc tgaagtaatt ggaactgctt ttgctctaaa catgctgttc     300
agaatcccag tatggtgtgg tgttctaata actggactca gcactctaat gctcttattg     360
ctgcagcaat atggggtccg taagctagaa tttctgattg catttctggt gttcttaata     420
acaacatgtt tcttagttga acttgggtat tct                                  453

<210> SEQ ID NO 3
<211> LENGTH: 2098
<212> TYPE: DNA
<213> ORGANISM: Zea mays

<400> SEQUENCE: 3
ggcacatcac tagctagtac agaaaatgga gcaggccggt gacgagacgc cgggagagat      60
cgggcgagag gctgctcgcc gtgaagctgc gctccggagc ggcggcggag acgccggaga     120
gcgcgtagac aaggctgtgg tggacggcgg agaagacgag cggtttcgcg tgcagcggaa     180
atggaggcgg ttcttggccc atgtcgggcc cggagctctc gtggccattg gcttcctgga     240
tcctagcaac ttgaaaaccg acatgcaagc tggggctgac ttcaagtacc agcttctgtg     300 ggtgattta tcgggatgg tcttcgcgct tctgatccaa acactggccg ccaaccttgg     360
agtgaagaca ggcaagcatc tcgctgagct ctgcaggaa gagtacccac gttccgtcaa     420
catctgcctg tggatcatcg cggagctggc ggtgatatcc gacgacatcc ccgaaggttg     480
ctgatcgatt aggcaatcag ctagctagct agcttccttc ctcctcgagt tcttcttctt     540
ctccttcttc ttcctgtcat cctgtacgtg tgtgtgctct aaacgatgcc cagctacctt     600
tggtttcact ttcacctacc gcagtgctgg gcacagcctt cgcgttcaac atcctgctcg     660
ggatcccggt gtgggccgga gtcgtcctca cggtgctcag cacgctgctg ctcctcgggg     720
tggagagatt cggggcccgc aagctggagt tcgtcgtggc agctttcatg ttcgccatgg     780
cggcctgctt cttcggggag ctgagctacc tgaggccgtc cgcggggga gttgtcgagg     840 gcatgttcgt ccccaggctc cgagggaaag gcgcggcagc caacgccatc cgctcttcg     900 gcgccatcat cacgccgtac aacctgttcc tgcactcggc gcttgtgctc tccaggaaga     960 cccgcggtc agtgaaaagc atcagggccg cgtgcaggta cttcctcgtg gagtgcagcc    1020
tggcgttcgt ggtggcgttc ctcatcaacg tggcggtggt cgtcgtcgcc gggtccatct    1080
gcaacgcggc gggcggcaac ctgtccccgg ccgacgcggc cgcgtgcggc gacctcactc    1140
tgcagtccac gcctctgctg ctcagggacg ttctggggag gtcgagctcc gtcgtgtacg    1200
ccgtcgcgct gctggcgtcc gggcagagca ccaccatcag ctgcacgttt gccgggcagg    1260
ttatcatgca ggggttcctg gacatgagga tgaagagctg ggtgcggaac ctgaccacgc    1320
gcgccatcgc catcgccccc agcctcgtcg tctccatcgt cagcggcccg tcgggtgctg    1380
gcaagctcat cgtcttctcg tcgatggtgc tgtcgttcga gctgccattc gcgctcatcc    1440
cgctcctcaa gttctgcaac agcagcaaca aagtcgggcc cctcaaggag tccatctaca    1500
cggtggtgat cgcgtgggcg ctgagcttcg cgctcatcgt ggtgaacacc tacttcctgg    1560
tgtggacgta cgtggactgg ctggtgcaca gtcggctccc caagtacgcc accgcgctcc    1620
```

```
tctccgtcgc cgtcctggcg ctcatggccg cctacctcgc cttcgtcgtc tacctggcgt    1680
tcaggaggga cgcggtgcgc acgtacgtgc cggtgtcgga gcgggcggag acggcagcg     1740 ggtcgcaggc ggtggcggcg gcggcctccg ccgacgacgc tgacatgccg gcgccgttca    1800
ggaaggacct ggctgatgct ccacgtaga cacggagatg ctctcgttcg ggcagtgacc     1860
atatcgatca atcctgttca tgcatatgat ttgtggatcg tcgtcgagag gcgtgctggc    1920
tcattcgtct gctcagtgac cgaatttgtt cgtgtacgta gattatcata agatcttaca    1980
cgcagccgca taccaagcca cacgaaccta cgtgtacggt tttgatatat cccatatcca    2040
acagttcatc catgttttac aatatagata atattattcg caaaaaaaaa aaaaaaa      2098
```

```
<210> SEQ ID NO 4
<211> LENGTH: 188
<212> TYPE: DNA
<213> ORGANISM: Zea mays
<220> FEATURE:
<221> NAME/KEY: unsure
<222> LOCATION: (152)
<223> OTHER INFORMATION: Nucleotide at this position may be a or g
      or t or c.
<220> FEATURE:
<221> NAME/KEY: unsure
<222> LOCATION: (170)
<223> OTHER INFORMATION: Nucleotide at this position may be a or g
      or t or c.
<220> FEATURE:
<221> NAME/KEY: unsure
<222> LOCATION: (173)
<223> OTHER INFORMATION: Nucleotide at this position may be a or g
      or t or c.
<220> FEATURE:
<221> NAME/KEY: unsure
<222> LOCATION: (175)
<223> OTHER INFORMATION: Nucleotide at this position may be a or g
      or t or c.
<220> FEATURE:
<221> NAME/KEY: unsure
<222> LOCATION: (182)
<223> OTHER INFORMATION: Nucleotide at position 182 may be a or g
      or t or c.

<400> SEQUENCE: 4
gtgccaccgc gctgccggcg gcccgcctcg ccagagtggt ggccgcctcc gaaagcggag    60
gcgcgactcc tccgagggcg tcccctcggc gggggcggcg cggcaagccc gggttctctc    120
ggcgttcggc aatcaagaag agcttccacc angagcaggt cgttgttttn cantnccgtc    180 tncaacga                                                            188

<210> SEQ ID NO 5
<211> LENGTH: 311
<212> TYPE: DNA
<213> ORGANISM: Zea mays
<220> FEATURE:
<221> NAME/KEY: unsure
<222> LOCATION: (7)
<223> OTHER INFORMATION: Nucleotide at this position may be a or g
      or c or t.
<220> FEATURE:
<221> NAME/KEY: unsure
<222> LOCATION: (10)
<223> OTHER INFORMATION: Nucleotide at this position may be a or g
      or c or t.
<220> FEATURE:
<221> NAME/KEY: unsure
<222> LOCATION: (69)
<223> OTHER INFORMATION: Nucleotide at this position may be a or g
      or c or t.
<220> FEATURE:
<221> NAME/KEY: unsure
```

```
<222> LOCATION: (109)
<223> OTHER INFORMATION: Nucleotide at this position may be a or g
      or t or c.
<220> FEATURE:
<221> NAME/KEY: unsure
<222> LOCATION: (204)
<223> OTHER INFORMATION: Nucleotide at this position may be a or g
      or t or c.
<220> FEATURE:
<221> NAME/KEY: unsure
<222> LOCATION: (230)
<223> OTHER INFORMATION: Nucleotide at this position may be a or g
      or t or c.
<220> FEATURE:
<221> NAME/KEY: unsure
<222> LOCATION: (257)
<223> OTHER INFORMATION: Nucleotide at this position may be a or g
      or t or c.
<220> FEATURE:
<221> NAME/KEY: unsure
<222> LOCATION: (309)
<223> OTHER INFORMATION: Nucleotide at this position may be a or g
      or t or c.

<400> SEQUENCE: 5
gcagcancan caagatgggg ccccacaaga actccatcta tatcatcgtg ttctcgtggc      60
tgctggggnt gatgatcatc ggcatcaaca tgtacttcct gaacaccanc ttcgtggggt    120
ggctcgtcca caactcgctc cccaagtacg ccaacgtgct cgtcggcctg ctcgtcttcc    180
ccctcatgct cgtctacgtc gtcnccgtca tctacctcac cttcaggaan gaaaccgtcg    240
tcaccttcgt cgccgantcc gcccagctgg gcgtggtcga acccaaaaa aggcaacaaa     300 ggcggggggng g                                                        311

<210> SEQ ID NO 6
<211> LENGTH: 471
<212> TYPE: DNA
<213> ORGANISM: Zea mays
<220> FEATURE:
<221> NAME/KEY: unsure
<222> LOCATION: (225)
<223> OTHER INFORMATION: Nucleotide at this position may be a  or g
      or t or c.
<220> FEATURE:
<221> NAME/KEY: unsure
<222> LOCATION: (256)
<223> OTHER INFORMATION: Nucleotide at this position may be a or g
      or t or c.
<220> FEATURE:
<221> NAME/KEY: unsure
<222> LOCATION: (336)
<223> OTHER INFORMATION: Nucleotide at this position may be a or g
      or t or c.
<220> FEATURE:
<221> NAME/KEY: unsure
<222> LOCATION: (383)
<223> OTHER INFORMATION: Nucleotide at this position may be a or g
      or t or c.
<220> FEATURE:
<221> NAME/KEY: unsure
<222> LOCATION: (418)
<223> OTHER INFORMATION: Nucleotide at this position may be a or g
      or t or c.
<220> FEATURE:
<221> NAME/KEY: unsure
<222> LOCATION: (428)
<223> OTHER INFORMATION: Nucleotide at this positon may be a or g
      or t or c.
<220> FEATURE:
<221> NAME/KEY: unsure
<222> LOCATION: (466)
<223> OTHER INFORMATION: Nucleotide at this position may be a or g
      or c or t.
<220> FEATURE:
```

<221> NAME/KEY: unsure
<222> LOCATION: (470)
<223> OTHER INFORMATION: Nucleotide at this position may be a or g
    or c or t.

<400> SEQUENCE: 6
cttcgacgtg aaaagagacc gtctgttccg aggttttgct tccatgtcga cgagaggcgg    60
cgaggccgcg aggcaggcga cggtgaagat catcgagacg tgcacgtgg aggcggaccg    120 gtacagcttc aagtccatcg tccagaggct cacggggaga gacgcggtgg tcggcggcgg    180
cggcgactac tcggaagggc gcccgaccgt ggatcatatg aagangcggc ggcgcacggg    240
gctgctgggt ttacgngcaa gcaagcgagc aggccctttc gctgattcgc cacgctgtta    300
aagacgagag ctgttgatgt tccatctgta aattgntttc ttttttttgg aactttggaa    360
tcagcgctcc atatagatac tanggtgtat ttggttcaac caaccaattg tagattangg    420
aaaacccnat atatttccac tagtttcaat tgaaaaaaaa aaggnaaan g              471

<210> SEQ ID NO 7
<211> LENGTH: 374
<212> TYPE: DNA
<213> ORGANISM: Zea mays
<220> FEATURE:
<221> NAME/KEY: unsure
<222> LOCATION: (112)
<223> OTHER INFORMATION: Nucleotide at this position may be a or g
    or t or c.
<220> FEATURE:
<221> NAME/KEY: unsure
<222> LOCATION: (336)
<223> OTHER INFORMATION: Nucleotide at this position may be a or g
    or c or t.
<220> FEATURE:
<221> NAME/KEY: unsure
<222> LOCATION: (367)
<223> OTHER INFORMATION: Nucleotide at this position may be a or g
    or t or c.
<220> FEATURE:
<221> NAME/KEY: unsure
<222> LOCATION: (373)
<223> OTHER INFORMATION: Nucleotide at this position may be a or g
    or c or t.

<400> SEQUENCE: 7
gcggagacgc cgagagcgcg tagacaaggc tgtggtggac ggcggagaag acgagcggtt    60
tcgcgtgcag cggaaaatgg aggcggttct tgggcccatgt cgggcccgga gntctcgtgg   120
ccattggctt cctggatcct agcaacttgg aaaccgacat gcaagctggg gctgacttca    180
agtaccagct tctgtgggtg attttagtcg ggatggtctt cgcgcttctg atccaaacac    240
tggccgccaa actttgagtg aagacaggca agcatcgctg agctctgcaa gggaagagta    300
acccaagttt ccgtcaacat ctgcctgttg gatcantcgc ggactggccg tgatatccga    360
cgacatnccc gant                                                      374

<210> SEQ ID NO 8
<211> LENGTH: 458
<212> TYPE: DNA
<213> ORGANISM: Zea mays
<220> FEATURE:
<221> NAME/KEY: unsure
<222> LOCATION: (18)
<223> OTHER INFORMATION: Nucleotides at this position may be a or
    g or c or t.
<220> FEATURE:
<221> NAME/KEY: unsure
<222> LOCATION: (297)

<223> OTHER INFORMATION: Nucleotide at this position may be a or
     g or c or t.
<220> FEATURE:
<221> NAME/KEY: unsure
<222> LOCATION: (371)
<223> OTHER INFORMATION: Nucleotide at this position may be a or
     g or c or t.
<220> FEATURE:
<221> NAME/KEY: unsure
<222> LOCATION: (372)
<223> OTHER INFORMATION: Nucleotide at this position may be a or
     g or c or t.
<220> FEATURE:
<221> NAME/KEY: unsure
<222> LOCATION: (392)
<223> OTHER INFORMATION: Nucleotide at this position may be a or
     g or c or t.
<220> FEATURE:
<221> NAME/KEY: unsure
<222> LOCATION: (454)
<223> OTHER INFORMATION: Nucleotide at this position may be a or
     g or c or t.
<220> FEATURE:
<221> NAME/KEY: unsure
<222> LOCATION: (456)
<223> OTHER INFORMATION: Nucleotide at this position may be a or
     g or c or t.

<400> SEQUENCE: 8

```
gcaagttgaa tggcaggntg ttttatgatg catattactc gaggcatttg atgttgatca      60
gaagtaatca agcatttgct tgcttgcaac attagtttgt ttagctgtta gatatgaaaa     120
gtacagaaaa taaattagta cataactctt agatttgcaa tgaacaagct tgggcttatg     180
agtttcagtg ccaacctcca aggttctctt ggtcagctag attgcagaga aaaaggacag     240
atacgggggg tttttagatc ttcggatgaa accctggata cgcaatcttg tcacgangtc     300
cttggctatc ctgccaagtt tgatcgtgtc aataatgggt gggtcctcca gcagctggcc     360
atttgattat nnattggatc gatgatactg gncattgaac tccccttttg gcttaggtcc     420
actcccctaa aattcaccag gagcaaaacc aagntngg                             458
```

<210> SEQ ID NO 9
<211> LENGTH: 182
<212> TYPE: DNA
<213> ORGANISM: Zea mays
<220> FEATURE:
<221> NAME/KEY: unsure
<222> LOCATION: (125)
<223> OTHER INFORMATION: Nucleotide at this position may be a or
     g or c or t.
<220> FEATURE:
<221> NAME/KEY: unsure
<222> LOCATION: (126)
<223> OTHER INFORMATION: Nucleotide at this position may be a or
     g or c or t.
<220> FEATURE:
<221> NAME/KEY: unsure
<222> LOCATION: (162)
<223> OTHER INFORMATION: Nucleotide at this position may be a or
     g or c or t.
<220> FEATURE:
<221> NAME/KEY: unsure
<222> LOCATION: (170)
<223> OTHER INFORMATION: Nucleotide at this position may be a or
     g or c or t.

<400> SEQUENCE: 9

```
ttgcatatat tgatcctgga aatttgagac ggatctacag gctgggagca caatacaaat      60
atgactcctt tggatcatac ttgttgcatc ctgtgctgtc ttattatcca accacttgca     120
```

-continued

```
gccanntagt tttgtgacaa ggaaaatctg caaacatgca gngttgaatn ccaagtcaca        180
at                                                                      182
```